United States Patent [19]

Takesue et al.

[11] Patent Number: 5,629,421
[45] Date of Patent: May 13, 1997

[54] HYDRAZONE COMPOUNDS

[75] Inventors: Atsushi Takesue; Yasuo Murakami; Takanobu Watanabe; Mitsutoshi Anzai, all of Ibaraki, Japan

[73] Assignee: Hodagaya Chemical Co., Ltd., Tokyo, Japan

[21] Appl. No.: 588,331

[22] Filed: Jan. 18, 1996

Related U.S. Application Data

[62] Division of Ser. No. 356,126, Dec. 15, 1994, Pat. No. 5,512,400.

[30] Foreign Application Priority Data

Dec. 15, 1993 [JP] Japan ................................. 5-342273
Oct. 12, 1994 [JP] Japan ................................. 6-271845

[51] Int. Cl.$^6$ ..................... C07D 223/26; C07D 223/28
[52] U.S. Cl. .............................. 540/591; 540/592
[58] Field of Search .............................. 540/591, 592

[56] References Cited

U.S. PATENT DOCUMENTS 4,456,671  6/1984  Mabuchi et al. ........................ 430/58

*Primary Examiner*—Philip I. Datlow
*Attorney, Agent, or Firm*—Oblon, Spivak, McClelland, Maier & Neustadt, P.C.

[57] ABSTRACT

There are provided a hydrazone compound represented by formula (I), an electrophotographic photoreceptor which has a photosensitive layer containing the compound on an electrically conductive support, and an organic electroluminescent element containing the compound as a charge transporting material:

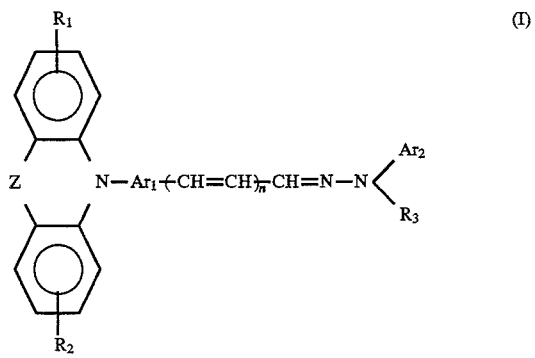

wherein $Ar_1$ represents a substituted or unsubstituted phenylene group, a substitued or unsubstituted naphthylene group, a substitued or unsubstituted biphenylene group, or a substituted or unsubstituted anthrylene group, $Ar_2$ represents a substituted or unsubstituted aryl group, $R_1$ and $R_2$ each independently represents a hydrogen atom, a halogen atom, an unsubstituted alkyl group, or an unsubstituted alkoxy group, $R_3$ represents an unsubstituted alkyl group, a substituted or unsubstituted aralkyl group, or a substituted or unsubstituted aryl group, Z represents an ethylene group or a vinylene group, and n is 0 or 1.

1 Claim, 5 Drawing Sheets

HYDRAZONE COMPOUNDS

This is a Division of application Ser. No. 08/356,126 filed on Dec. 15, 1994 now U.S. Pat. No. 5,512,400.

FIELD OF THE INVENTION

The present invention relates to a novel hydrazone compound useful as a charge transporting material for use in an electrophotographic photoreceptor, an organic electroluminescent element, and the like. The present invention also relates to an electrophotographic photoreceptor and an organic electroluminescent element both containing the hydrazone compound.

BACKGROUND OF THE INVENTION

Electrophotography is a kind of image-forming process, which generally comprises charging the surface of a photoreceptor containing a photoconductive material in the dark by means of, e.g., corona discharge, image-wise exposing the resulting photoreceptor to selectively eliminate the charge in the exposed area to thereby obtain an electrostatic latent image, converting the latent image into a visible image using a toner, transferring the toner image to paper, etc., and then fixing the toner particles to obtain an image.

Photoreceptors include inorganic photoreceptors containing an inorganic photoconductive compound, e.g., selenium, zinc oxide, cadmium sulfide, or silicon, as a major component and organic photoreceptors containing an organic charge generation material and a low- or high-molecular organic charge transporting material both of which are dispersed in a binder resin. The inorganic photoreceptors each has many advantages and has been widely used so far. However, those inorganic photoconductive compounds have the following drawbacks. For example, selenium not only is costly because of the difficulty of the production thereof, but also tends to crystallize and to be readily affected by heat or mechanical shock to thereby suffer performance deterioration. Zinc oxide and cadmium sulfide are insufficient in moisture resistance and mechanical strength, and a dye added as a sensitizer is deteriorated by the charging and exposure. Thus, photoreceptors containing zinc oxide or cadmium sulfide are defective in durability, etc. Silicon is also costly because of the difficulty of the production thereof and because a highly irritant gas is used for producing the same. Moreover, care should be taken in handling silicon because it is sensitive to moisture.

For the purpose of overcoming the drawbacks of these inorganic photoreceptors, organic photoreceptors containing various organic compounds have been investigated in recent years and have come to be used widely. The organic photoreceptors include single-layer photoreceptors in which both a charge generation material and a charge transporting material are dispersed in a binder resin and double-layered photoreceptors which comprise a charge generation layer and a charge transporting layer which layers perform their respective functions. Organic photoreceptors of the double-layer type are advantageous in that each material can be selected from a wide range of compounds and a photoreceptor having a desired performance can be produced relatively easily by selecting a suitable material combination. Because of this, a large number of investigations have been made on double-layered organic photoreceptors, which are in wide use.

As the charge generation materials, various kinds of organic pigments and dyes have been proposed and put to practical use. Examples thereof include azo compounds, bisazo compounds, trisazo compounds, tetrakisazo compounds, thiapyrylium salts, squarilium salts, azulenium salts, cyanine dyes, perylene compounds, metal-free or metal phthalocyanine compounds, polynuclear quinone compounds, thioindigo compounds, and quinacridone compounds.

Examples of charge transporting materials include the oxadiazole compounds disclosed in JP-B-34-5466, the oxazole compounds disclosed in JP-A-56-123544, pyrazoline compounds disclosed in JP-B-52-41880, the hydrazone compounds disclosed in JP-B-55-42380, JP-B-61-40104, JP-B-62-35673, and JP-B-63-35976, the diamine compounds disclosed in JP-B-58-32372, stilbene compounds disclosed in JP-B-63-18738, JP-B-63-19867, and JP-B-3-39306, and the butadiene compounds disclosed in JP-A-62-30255. (The terms "JP-B" and "JP-A" as used herein mean an "examined Japanese patent publication" and an "unexamined published Japanese patent application," respectively.) Some of the organic photoreceptors containing these charge transporting materials have excellent properties and have come into practical use. However, any organic photoreceptor has not been obtained so far which fully satisfies the various property requirements which an electrophotographic photoreceptor is required to meet.

On the other hand, electroluminescent elements containing an organic compound as a component thereof have conventionally been investigated, but sufficient luminescent properties have not been obtained. In recent years, however, a multilayered electroluminescent element comprising several kinds of superposed organic materials was found to show significantly improved properties. Since then, investigations on electroluminescent elements containing organic substances have been made actively. The first multilayered electroluminescent element was reported by C. W. Tang et al. of Eastman Kodak Corp. (*Appl. Phys. Lett.* Vol. 51, p. 913 (1987)). In this electroluminescent element, a luminance of 1,000 $cd/m^2$ or higher was obtained at a voltage of 10 V or lower, showing that this organic electroluminescent element has far higher electroluminescent properties than the conventional inorganic electroluminescent elements in practical use, which inorganic elements need a voltage as high as 200 V or higher.

Such multilayered electroluminescent elements have a structure comprising superposed layers of an organic fluorescent substance, an organic substance capable of transporting charges, i.e., a charge transporting material, and electrodes. When charges (holes and electrons) are injected from each electrode, the charges move through the charge transporting material and recombine to cause luminescence. Used as the organic fluorescent substance are, for example, fluorescent organic dyes such as 8-quinolinol aluminum complex and coumarin. For use as the charge transporting material, various compounds well known as organic materials for use in electrophotographic photoreceptors are being investigated. Examples of such compounds for use as charge transporting materials include diamine compounds such as N,N'-di(3-tolyl)-N,N'-diphenyl-4,4'-diaminodiphenyl and 1,1-bis[N,N-di(4-tolyl)amino-phenyl]cyclohexane and hydrazone compounds such as 4-diphenyl-aminobenzaldehyde-N,N-diphenylhydrazone. Also used are porphyrin compounds such as copper phthalocyanine.

Although organic electroluminescent elements have high luminescent properties, they are insufficient in stability during luminescence and in storage stability and have hence not been put to practical use. As one of the causes of the insufficient stability during luminescence and storage of the element, the insufficient stability of the charge transporting material is considered. Since the organic layers of an organic electroluminescent element are as thin as from 50 to hundreds of nanometers, an exceedingly high voltage is applied per unit thickness. In addition, heat generation occurs due to luminescence and the application of an electric current. The charge transporting material is therefore required to have electrical, thermal, and chemical stability. Furthermore, the charge transporting layer of an element, which layer is generally in an amorphous state, undergoes crystallization due to luminescence or long-term storage, whereby luminescence is inhibited or element breakage is caused. For this reason, the charge transporting material is required to have the property of readily coming into an amorphous or vitreous state and stably retaining this state.

With respect to the compounds proposed for use as a charge transporting material, by which the stability of a luminescent element is affected as described above, the diamine compounds and the porphyrin compounds still have the problem that they undergo crystallization to cause element deterioration, although these compounds are electrically and thermally stable and some of these attain relatively high luminescent properties. The hydrazone compounds, which have a simple structure, are insufficient in electrical and thermal stability, so that they are not a desirable material.

A charge transporting material for use in an organic photoreceptor is required not only to enable the photoreceptor to satisfy various property requirements including sensitivity, but also to have chemical stability so as to withstand light, ozone, and electrical load and further have stability or durability so as not to cause a sensitivity decrease even when the photoreceptor is used repeatedly or over long.

A charge transporting material for use in an organic electroluminescent element is required not only to enable the element to satisfy various property requirements including luminescent properties, but also have good film-forming properties so as to impart excellent stability during luminescence and storage to the organic electroluminescent element and also have stability so as to withstand heat, oxygen, and electrical load.

SUMMARY OF THE INVENTION

An object of the present invention is to provide a novel hydrazone compound useful as a charge transporting material, with which an electrophotographic photoreceptor having satisfactory photoreceptor properties and high sensitivity and durability and an organic electroluminescent element excellent not only in luminescent property but in stability during luminescence and storage can be obtained.

Another object of the present invention is to provide an electrophotographic photoreceptor and an organic electroluminescent element both of which contain the hydrazone compound.

The present invention provides a hydrazone compound represented by the following formula (I), an electrophotographic photoreceptor which has a photosensitive layer containing the compound on an electrically conductive support, and an organic electroluminescent element containing the compound as a charge transporting material.

In formula (I), $Ar_1$ represents a substituted or unsubstituted phenylene group, a substituted or unsubstituted naphthylene group, a substituted or unsubstituted biphenylene group, or a substituted or unsubstituted anthrylene group, $Ar_2$ represents a substituted or unsubstituted aryl group, $R_1$ and $R_2$ each independently represents a hydrogen atom, a halogen atom, an unsubstituted alkyl group, or an unsubstituted alkoxy group, $R_3$ represents an unsubstituted alkyl group, a substituted or unsubstituted aralkyl group, or a substituted or unsubstituted aryl group, Z represents an ethylene group or a vinylene group, and n is 0 or 1.

DETAILED DESCRIPTION OF THE INVENTION

The hydrazone compound represented by formula (I) will be described in more detail below.

$Ar_1$ represents a phenylene group, a naphthylene group, a biphenylene group or a anthrylene group, which may have a substituent(s).

$Ar_2$ represents an aryl group which may have a substituent(s). Examples of the unsubstituted aryl group include a phenyl group, a naphthyl group, a biphenyl group, an anthryl group, and a pyrenyl group.

$R_1$ and $R_2$ each independently represents a hydrogen atom, a halogen atom, an unsubstituted alkyl group (preferably having 1 to 4 carbon atoms), or an unsubstituted alkoxy group (preferably having 1 to 4 carbon atoms).

$R_3$ represents an unsubstituted alkyl group (preferably having 1 to 6 carbon atoms), an aralkyl group which may have a substituent(s), or an aryl group which may have a substituent(s).

Examples of the substituent with respect to $Ar_1$, $Ar_2$ and $R_3$ described above include an alkyl group having 1 to 4 carbon atoms, an alkoxy group having 1 to 4 carbon atoms, a chlorine atom and a bromine atom.

The hydrazone compound represented by formula (I) described above, which may be used as a charge transporting material in the present invention, is a novel compound. In general, this compound is synthesized from the corresponding aldehyde compound and hydrazine compound through condensation. For example, the hydrazone compound can be obtained by reacting an aldehyde compound represented by the following formula (II):

(II)

(wherein $Ar_1$, $R_1$, $R_2$, Z, and n have the same meanings as in formula (I)) with a hydrazine derivative represented by the following formula (III):

(III)

(wherein $Ar_2$ and $R_3$ have the same meanings as in formula (I)) at a temperature of 10° to 120° C., preferably 25° to 80° C., in an organic solvent inert to the reactants, e.g., toluene, alcohol, acetone, N,N-dimethylformamide, dimethyl sulfoxide, tetrahydrofuran, or dioxane. If desired, use may be made of an acid catalyst such as p-toluenesulfonic acid, hydrochloric acid, sulfuric acid, or acetic acid or a reaction accelerator such as sodium acetate.

Alternatively, the hydrazone compound may be obtained by reacting an aldehyde compound represented by formula (II) described above with a hydrazine derivative represented by the following formula (IV):

(IV)

(wherein $Ar_2$ has the same meaning as in formula (I)) at a temperature of 10° to 120° C., preferably 25° to 80° C., in an organic solvent inert to the reactants, e.g., toluene, alcohol, acetone, N,N-dimethylformamide, dimethyl sulfoxide, tetrahydrofuran, or dioxane, if desired in the presence of an acid catalyst such as p-toluenesulfonic acid, hydrochloric acid, sulfuric acid, or acetic acid or a reaction accelerator such as sodium acetate, to thereby obtain a hydrazone compound represented by the following formula (V):

(V)

(wherein $Ar_1$, $Ar_2$, $R_1$, $R_2$, Z, and n have the same meanings as in formula (I)), and then reacting this hydrazone compound with an alkylating, aralkylating, or arylating agent represented by the following formula (VI):

$R_3X$ (VI)

(wherein $R_3$ has the same meaning as defined above and X represents a chlorine atom, a bromine atom, an iodine atom, and a sulfonic acid residue) at a temperature of 10° to 200° C., preferably 30° to 120° C., in an organic solvent inert to the reactants, e.g., toluene, xylene, dichlorobenzene, nitrobenzene, N,N-dimethylformamide, N-methylpyrrolidone, alcohol, or dioxane, in the presence of a deacidifying agent such as, e.g., sodium hydroxide, potassium hydroxide, sodium hydrogen carbonate, potassium hydrogen carbonate, sodium carbonate, potassium carbonate, triethylamine, or pyridine.

The following are examples of the compound of the present invention, which examples can be used as a charge transporting material.

Compound No. 1

Compound No. 2

Compound No. 3

Compound No. 8

Compound No. 4

Compound No. 9

Compound No. 5

Compound No. 10

Compound No. 6

Compound No. 11

Compound No. 7

Compound No. 12

-continued

Compound No. 13

Compound No. 18

Compound No. 14

Compound No. 19

Compound No. 15

Compound No. 20

Compound No. 16

Compound No. 21

Compound No. 17

Compound No. 22

-continued

Compound No. 23

Compound No. 24

Compound No. 25

Compound No. 26

Compound No. 27

Compound No. 28

-continued

Compound No. 29

Compound No. 30

Compound No. 31

Compound No. 32

The electrophotographic photoreceptor of the present invention has a photosensitive layer containing one or more hydrazone compounds represented by formula (I). The photosensitive layer of the electrophotographic photoreceptor of the present invention may have any of various possible constitutions. Photoreceptors having representative photosensitive-layer constitutions are shown in FIGS. 1 to 5.

Figure 1:
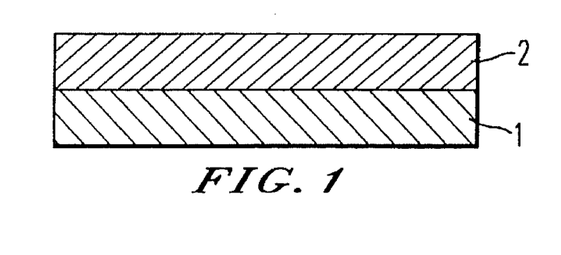
FIG. 1 is a sectional view of a single-layer electrophotographic photoreceptor.

The photoreceptor shown in FIG. 1 comprises a conductive support 1 and formed thereon a photosensitive layer 2 comprising the hydrazone compound, a sensitizing dye, and a binder resin.

Figure 2:
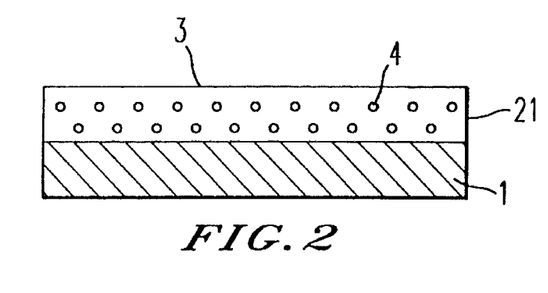
FIG. 2 is a sectional view of a single-layer electrophotographic photoreceptor containing a charge generation material dispersed therein.

The photoreceptor shown in FIG. 2 comprises a conductive support 1 and formed thereon a photosensitive layer 21 comprising a charge-transporting medium 3 comprising the hydrazone compound and a binder resin and a charge generation material 4 dispersed in a charge-transporting medium 3. In this photoreceptor, the charge generation material generates charges upon light absorption and the charges are transported by the charge-transporting medium. It is desirable that the charge transporting material does not absorb the light which the charge generation material absorbs to generate charges. The hydrazone compound shows only a little light absorption in part of the range of from the ultraviolet region to the low-wavelength visible region, and therefore satisfies the condition that its absorption wavelength region does not overlap with that of a charge generation material.

In the photoreceptors shown in FIGS. 1 and 2, the thickness of the photosensitive layer is preferably from 10 to 25 μm.

Figure 3:
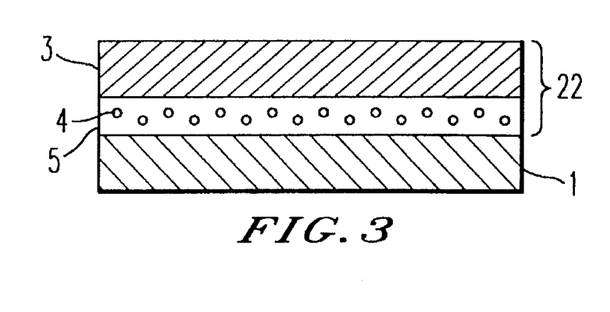
FIG. 3 is a sectional view of an electrophotographic photoreceptor comprising a charge generation layer and a charge transporting layer formed in this order on an electrically conductive support.

The photoreceptor shown in FIG. 3 comprises a conductive support 1 and formed thereon a photosensitive layer 22 made up of a charge generation layer 5 consisting mainly of a charge generation material 4 and a charge transporting layer 3 comprising the hydrazone compound and a binder resin. In this photoreceptor, the light which has passed through the charge transporting layer 3 reaches the charge generation layer 5, where the light is absorbed by the charge generation material 4 to generate charges. These charges are injected into the charge transporting layer 3 and transported.

Figure 4:
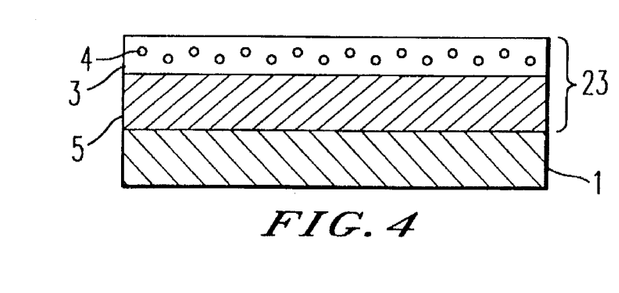
FIG. 4 is a sectional view of an electrophotographic photoreceptor comprising a charge transporting layer and a charge generation layer formed in this order on an electrically conductive support.

The photoreceptor shown in FIG. 4 has a photosensitive layer 23 which is the same as the photosensitive layer of the photoreceptor shown in FIG. 3 except that the positions of the charge generation layer 5 and the charge transporting layer 3 are reversed. The mechanism of charge generation and charge transportation in this photoreceptor is the same as in the above photoreceptor.

Figure 5:
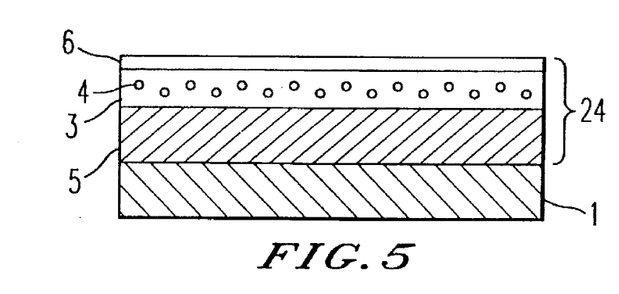
FIG. 5 is a sectional view of an electrophotographic photoreceptor having a protective layer.

The photoreceptor shown in FIG. 5 has a photosensitive layer 24 which is the same as the photosensitive layer of the photoreceptor shown in FIG. 4 except that it further has a protective layer 6 formed on the charge generation layer 5 for the purpose of improving mechanical strength.

In the photoreceptors shown in FIGS. 3, 4 and 5, the thickness of the charge generation layer is preferably 2 μm or less, and the thickness of the charge transporting layer is preferably 5 to 25 μm. The thickness of the protective layer is preferably 2 μm or less.

The amount of the hydrazone compound in the hydrazone compound-containing layer is generally from 30 to 70% by weight, preferably from 40 to 60% by weight.

The amount of the sensitizing dye in the photosensitive layer shown in FIG. 1 is generally from 0.1 to 5% by weight. The amount of the charge generation material in the photosensitive layer shown in FIG. 2 is generally from 1 to 30% by weight. The amount of the charge generation material in the charge generation layers shown in FIGS. 3, 4 and 5 is generally from 20 to 90% by weight. The sensitizing dye and electron-withdrawing compound each can be used generally in an amount of 0.1 to 5% by weight.

These photoreceptors according to the present invention may be produced by ordinary methods. For example, the hydrazone compound represented by formula (I) described above is dissolved in an appropriate solvent along with a binder resin. If desired, a charge generation material, a sensitizing dye, an electron-withdrawing compound, a plasticizer, a pigment, and other additives are added to the solution. The coating fluid thus prepared is applied to a conductive support and dried to form a photosensitive layer having a thickness of several micrometers to tens of micrometers to thereby produce a photoreceptor. A photosensitive layer having a double-layer structure comprising a charge generation layer and a charge transporting layer can be produced by applying the above-described coating fluid on a charge generation layer, or by forming a charge generation layer on a charge transporting layer formed from the above-described coating fluid by coating. If desired, an adhesive layer, an interlayer, or a barrier layer may be formed in the photoreceptors thus produced.

Examples of the charge generation material which can be used in the present invention include any conventional charge generation material such as azo compounds, bisazo compounds, trisazo compounds, tetrakisazo compounds, thiapyrylium salts, squarilium salts, azulenium salts, cyanine dyes, perylene compounds, metal-free or metal phthalocyanine compounds, polynuclear quinone compounds, thioindigo compounds, and quinacridone compounds Examples of the solvent which can be used for the preparation of the coating fluid include polar organic solvents such as tetrahydrofuran, 1,4-dioxane, methyl ethyl ketone, cyclohexanone, acetonitrile, N,N-dimethylformamide, and ethyl acetate, aromatic organic solvents such as toluene and xylene, and chlorinated hydrocarbon solvents such as dichloromethane and dichloroethane. Solvents in which the hydrazone compound and the binder resin are highly soluble are preferred.

Examples of the sensitizing dye include triarylmethane dyes such as Methyl Violet, Brilliant Green, Crystal Violet, and Acid Violet, xanthene dyes such as Rhodamine B, Eosine S, and Rose Bengale, thiazine dyes such as Methylene Blue, pyrylium dyes such as benzopyrylium salts, thiapyrylium dyes, and cyanine dyes.

Examples of the electron-withdrawing compound which forms a charge transfer complex in cooperation with the hydrazone compound include quinones, e.g., chloranil, 2,3-dichloro-1,4-naphthoquinone, 1-nitroanthraquinone, 2-chloroanthraquinone, and phenanthrenequinone, aldehydes, e.g., 4-nitrobenzaldehyde, ketones, e.g., 9-benzoylanthracene, indandione, 3,5-dinitrobenzophenone, 2,4,7-trinitrofluorenone, and 2,4,5,7-tetranitrofluorenone, acid anhydrides, e.g., phthalic anhydride and 4-chloronaphthalic anhydride, cyano compounds, e.g., tetracyanoethylene, terephthalalmalenonitrile, and 9-anthrylmethylidenemalenonitrile, and phthalide derivatives, e.g., 3-benzalphthalide and 3-(α-cyano-p-nitrobenzal)-4,5,6,7-tetrachlorophthalide.

Examples of the binder resin include various resins compatible with the hydrazone compound, such as homopolymers and copolymers of vinyl compounds, e.g., styrene, vinyl acetate, vinyl chloride, acrylic esters, methacrylic esters, and butadiene, poly(vinyl acetal)s, polycarbonates, polyesters, poly(phenylene oxide)s, polyurethanes, cellulose esters, phenoxy resins, silicon resins, and epoxy resins. The binder resin is used in an amount of usually from 0.4 to 10 times by weight, preferably from 0.5 to 5 times by weight, the amount of the hydrazone compound.

A known plasticizer may be incorporated into the photosensitive layer of the present invention for the purpose of improving film-forming properties, flexibility, and mechanical strength. Examples of the plasticizer include phthalic esters, phosphoric esters, chlorinated paraffins, methylnaphthalene, epoxy compounds, and chlorinated fatty esters.

The conductive support on which the photosensitive layer is formed may be a material for use as the support of a known electrophotographic photoreceptor. Examples of the support include drums or sheets of a metal, e.g., aluminum, stainless steel, or copper; substrates obtained by laminating or vapor-depositing such a metal; plastic films or drums and paper sheets or tubes to each of which electrical conductivity has been imparted by coating with a conductive substance, e.g., a metal powder, carbon black, copper iodide, or a polymeric electrolyte, along with an appropriate binder; and plastic films or drums to each of which electrical conductivity has been imparted by incorporating such a conductive substance.

According to the present invention, an organic electroluminescent element is also obtained which contains the hydrazone compound represented by the above-described formula (I) as a hole-transporting layer.

Organic electroluminescent elements have a two-layer or three-layer structure sandwiched between a transparent electrode serving as a base and a counter electrode. The two-layer structure is a combination of a hole-transporting layer and an electron-transporting luminescent layer or a combination of an electron-transporting layer and a hole-transporting luminescent layer. The three-layer structure comprises a luminescent layer sandwiched between a hole-transporting layer and an electron-transporting layer.

The layer constitution according to the present invention may be either a two-layer structure comprising a hole-transporting layer and an electron-transporting luminescent layer (as a luminescent layer) or a three-layer structure comprising a hole-transporting layer, an electron-transporting luminescent layer or an hole-transporting luminescent layer (as a luminescent layer), and an electron-transporting layer. Each layer generally has the thickness of 20 to 300 nm.

The hole-transporting layer is made of the hydrazone compound of formula (I) of the present invention and has a thickness of generally from 20 to 300 nm, preferably from 30 to 200 nm.

Figure 6:
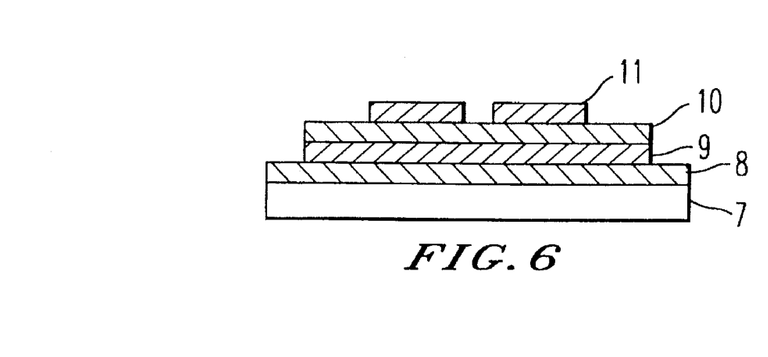
FIG. 6 is a sectional view of an organic electroluminescent element.

FIG. 6 shows an organic electroluminescent element having the two-layer structure.

The organic electroluminescent element shown in FIG. 6 comprises a support 7 and, formed thereon in this order, a transparent electrode 8, a hole-transporting layer 9, an electron-transporting luminescent layer 10, and an electrode 11.

Examples of an electron-transporting luminescent material include chelated oxinoide compounds, e.g., tris(8-quinolinol)aluminum, bis(8-quinolinol)magnesium, and tris(5-chloro-8-quinolinol)gallium, coumarin derivatives, perylene pigments, chelated 2,2'-bipyridine compounds, and chelate compounds of salicylidene-o-aminophenol derivatives.

Examples of an electron transporting material include 2-(4-tert-butylphenyl)-5-(4-biphenylyl)-1,3,5-oxadiazole, 2,4,7-trinitro-9-fluorenone, 4-butoxycarbonyl-9-dicyanomethylidene-fluorene, 3,3'-bis(tert-butyl)-5,5'-dimethyl-4,4'-diphenoquinone, 3,5'-bis(tert-butyl)-5,3'-dimethyl-4,4'-diphenoquinone, and 3,5-bis(tert-butyl)-3',5'-dimethyl-4,4'-diphenoquinone.

Examples of a hole-transporting luminescent material include 4,4'-bis(2,2-diphenylvinyl)biphenyl 4-styryl-4',4''-dimethoxytriphenylamine and 4,4'-bis[5-(p-dimethylaminophenyl)-1,3,4-oxadiazol-2-yl]biphenyl.

The support of the organic electroluminescent element may be a glass, a plastic, quartz, etc. A metal, e.g., gold, aluminum, indium, silver, or magnesium, an indium-tin oxide (ITO), tin oxide, zinc oxide, or the like is deposited as a thin layer on the support by vapor deposition to give a translucent or transparent electrode. A charge transporting layer (i.e., a hole-transporting layer and a electron-transporting layer) and a luminescent layer are formed on the electrode by vapor deposition, and another electrode is further formed thereon in the same manner as the above to thereby produce an organic electroluminescent element. This element is caused to luminesce by applying a direct voltage thereto.

The present invention will be explained below in more detail by reference to the following Examples, but the invention should not be construed as being limited thereto. Otherwise indicated, all parts and percentage are by weight.

EXAMPLE 1

Synthesis of Compound No. 2

In 500 parts of tetrahydrofuran were dissolved 29.9 parts of 4-[5-(10,11-dihydro-5H-dibenzo[b,f]azepinyl)]benzaldehyde and 24.3 parts of N,N-diphenylhydrazine hydrochloride. This solution was stirred at 50° C. for 2 hours. After completion of the reaction, the reaction mixture was poured into 2,000 parts of water, and the crystals precipitated were taken out by filtration. The crystals obtained were washed with ethyl alcohol and then dried at reduced pressure. These crystals were purified by columnchromatography (carrier, silica gel; eluent, toluene/hexane=½ by volume) to obtain 27.3 parts (yield, 58.6%) of 4-[5-(10,11-dihydro-5H-dibenzo[b,f]-azepinyl)]benzaldehyde N,N-diphenylhydrazone. This compound had a melting point of 196.0° to 197.0° C. The results of elemental analysis are shown in Table 1 below, together with calculated values for $C_{33}H_{27}N_3$.

TABLE 1

| | C (%) | H (%) | N (%) |
|---|---|---|---|
| Calculated value | 85.1 | 5.8 | 9.0 |
| Found value | 85.3 | 6.0 | 9.2 |

Figure 7:
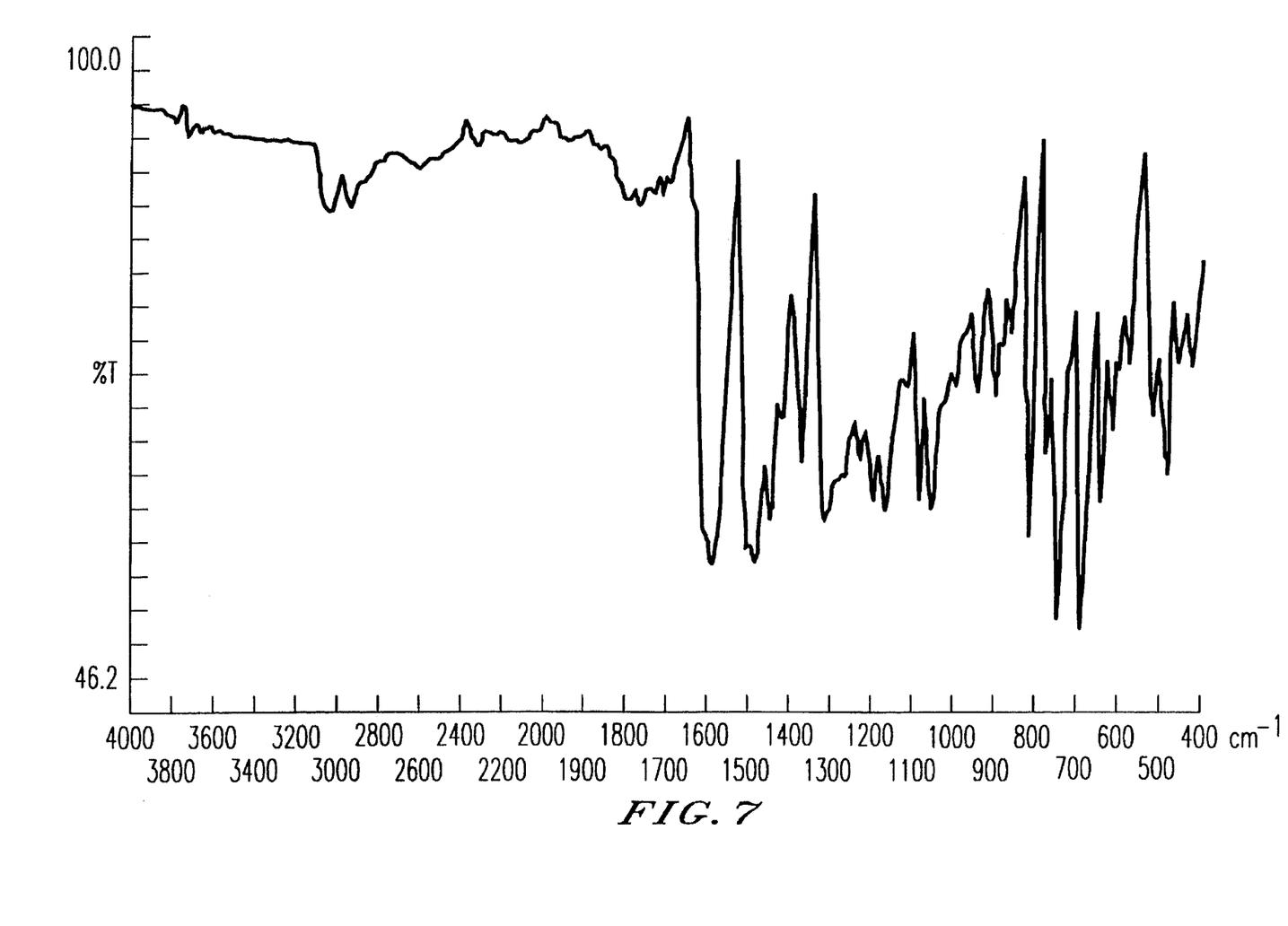
FIG. 7 is an infrared absorption spectrum of Compound No. 2.

The infrared absorption spectrum (KBr tablet method) of the compound obtained is shown in FIG. 7.

EXAMPLE 2

Synthesis of Compound No. 17

In 500 parts of tetrahydrofuran were dissolved 29.7 parts of 4-[5-(5H-dibenzo[b,f]azepinyl)]benzaldehyde and 13.4 parts of N,N-methylphenylhydrazine. One part of glacial acetic acid was added thereto, and this solution was stirred at 50° C. for 3 hours. After completion of the reaction, the reaction mixture was poured into 2,000 parts of water, and the crystals precipitated were taken out by filtration. The crystals obtained were washed with ethyl alcohol and then dried at reduced pressure. The crystals dried were recrystallized from ethyl acetate to obtain 28.9 parts (yield, 72.0%) of 4-[5-(5-H-dibenzo[b,f]azepinyl)]benzaldehyde N,N-methylphenylhydrazone. This compound had a melting point of 195.0° to 197.0° C. The results of elemental analysis are shown in Table 2 below, together with calculated values for $C_{28}H_{23}N_3$.

TABLE 2

|  | C (%) | H (%) | N (%) |
|---|---|---|---|
| Calculated value | 83.8 | 5.8 | 10.5 |
| Found value | 83.4 | 6.1 | 10.3 |

Figure 8:
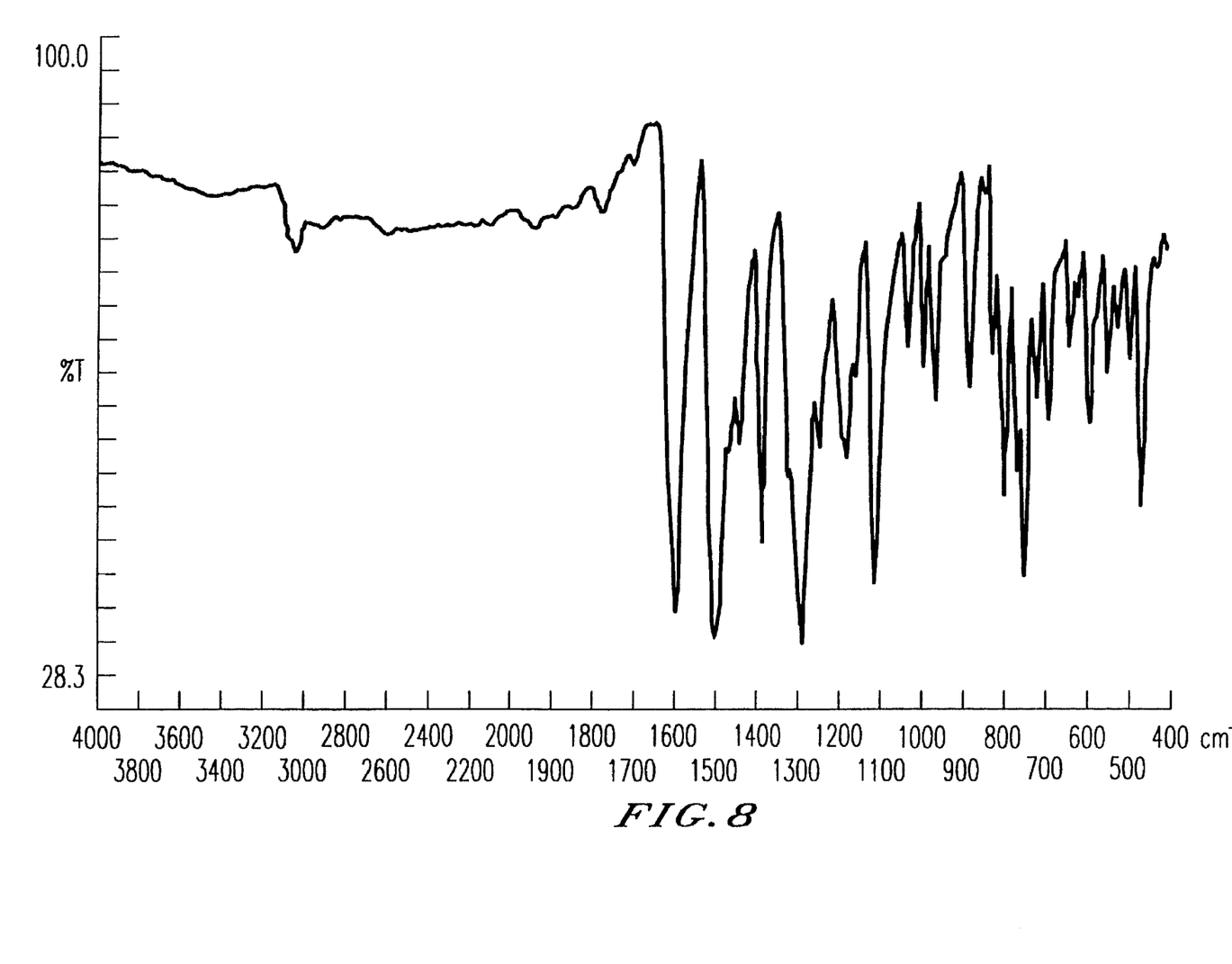
FIG. 8 is an infrared absorption spectrum of Compound No. 21.

The infrared absorption spectrum (KBr tablet method) of the compound obtained is shown in FIG. 8.

EXAMPLE 3

Synthesis of Compound No. 1

In 500 parts of tetrahydrofuran were dissolved 21.0 parts of 4-[5-(10,11-dihydro-5H-dibenzo[b,f]azepinyl)]benzaldehyde and 12.0 parts of N,N-methylphenylhydrazine. One part of glacial acetic acid was added thereto, and this solution was stirred at room temperature for 3 hours. After completion of the reaction, the reaction mixture was poured into 2,000 parts of water, and the crystals precipitated were taken out by filtration. The crystals obtained were washed with ethyl alcohol and then dried at reduced pressure. These crystals were purified by column chromatography (carrier, silica gel; eluent, toluene/hexane=2/3 by volume) to obtain 15.8 parts (yield, 55.8%) of 4-[5-(10,11-dihydro-5H-dibenzo[b,f]-azepinyl)]benzaldehyde N,N-methylphenylhydrazone. This compound had a melting point of 192.0° to 194.0° C. The results of elemental analysis are shown in Table 3 below, together with calculated values for $C_{28}H_{25}N_3$.

TABLE 3

|  | C (%) | H (%) | N (%) |
|---|---|---|---|
| Calculated value | 83.3 | 6.3 | 10.4 |
| Found value | 83.4 | 6.4 | 10.4 |

Figure 9:
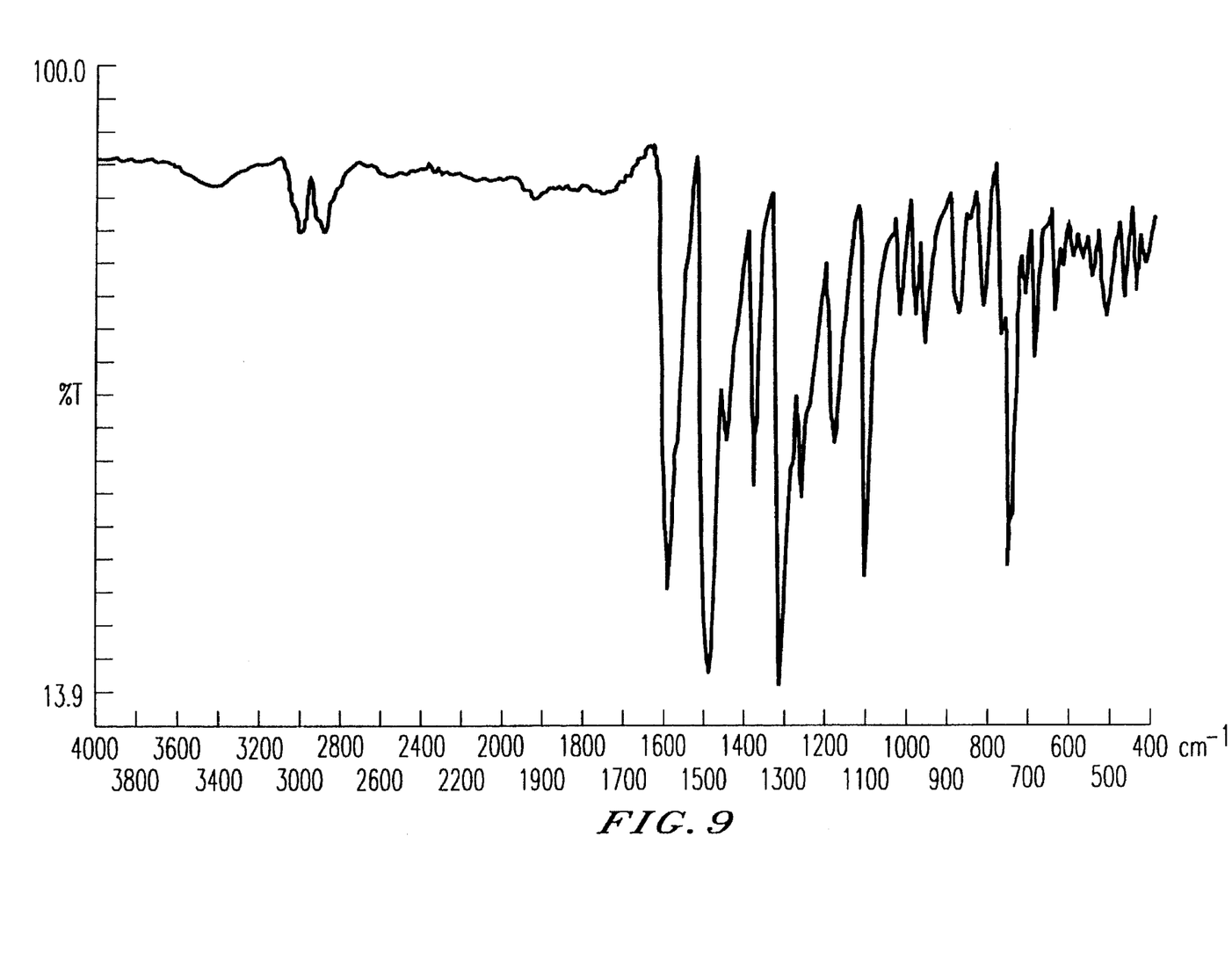
FIG. 9 is an infrared absorption spectrum of Compound No. 1.

The infrared absorption spectrum (KBr tablet method) of the compound obtained is shown in FIG. 9.

EXAMPLE 4

Synthesis of Compound No. 18

In 500 parts of tetrahydrofuran were dissolved 23.8 parts of 4-[5-(5H-dibenzo[b,f]azepinyl)]benzaldehyde and 26.5 parts of N,N-diphenylhydrazine hydrochloride. This solution was stirred at room temperature for 3 hours. After completion of the reaction, the reaction mixture was poured into 2,000 parts of water, and the crystals precipitated were taken out by filtration. The crystals obtained were washed with ethyl alcohol and then dried at reduced pressure. The crystals dried were dissolved in 100 parts of ethyl acetate, and this solution was poured into 1,000 pats of methyl alcohol to recrystallize the reaction product. Thus, 28.9 parts (yield, 77.9%) of 4-[5-(5H-dibenzo[b,f]azepinyl)]benzaldehyde N,N-diphenylhydrazone was obtained. This compound had a melting point of 178.0° to 179.0° C. The results of elemental analysis are shown in Table 4 below, together with calculated values for $C_{33}H_{25}N_3$.

TABLE 4

|  | C (%) | H (%) | N (%) |
|---|---|---|---|
| Calculated value | 85.5 | 5.4 | 9.1 |
| Found value | 85.3 | 5.6 | 9.0 |

Figure 10:
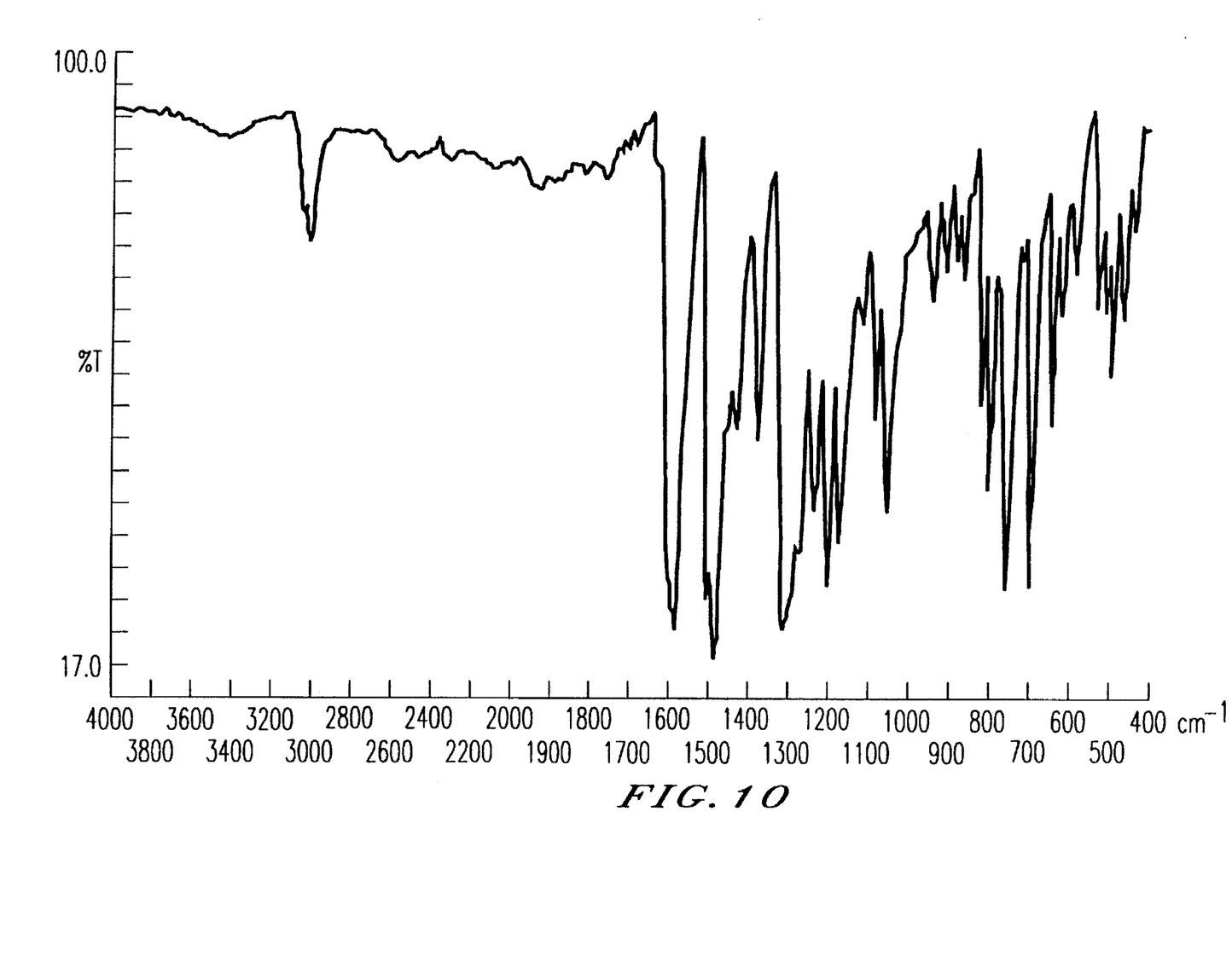
FIG. 10 is an infrared absorption spectrum of Compound No. 22.

The infrared absorption spectrum (KBr tablet method) of the compound obtained is shown in FIG. 10.

EXAMPLE 5

To 18.5 parts of an 8% THF solution of a polyester resin (Vylon 200, manufactured by Toyobo Co., Ltd., Japan) was added, as a charge generation material, 1.5 parts of Chlorodiane Blue (Compound A) having the following structure.

Compound A

This mixture was placed in an agate pot containing agate balls, and this pot was rotated for 1 hour in a planetary grinder (manufactured by Fritsch Co.) to disperse the charge generation material. An aluminum-deposited PET film serving as a conductive support was coated on the aluminum side with the above-obtained dispersion by means of a wire-wound bar coater. The coating was dried first at 60° C. and ordinary pressure for 2 hours and then at reduced pressure for 2 hours to form a charge generation layer having a thickness of 0.3 μm.

On the other hand, 1.5 parts of Compound No. 1 as a charge transporting material was added to 18.75 parts of an 8% dichloroethane solution of a polycarbonate resin (Panlite K-1300, manufactured by Teijin Chemicals Ltd., Japan). Ultrasonic wave was applied to this mixture to completely dissolve the hydrazone compound. This solution was applied to the charge generation layer with a wire-wound bar coater, and the coating was dried first at 60° C. and ordinary pressure for 2 hours and then at reduced pressure for 2 hours to form a charge transporting layer having a thickness of about 20 μm. Thus, photoreceptor No. 1 was produced.

The sensitivity of this photoreceptor was measured with an electrostatic copying paper tester (trade name "EPA-8100," manufactured by Kawaguchi Denki Seisakusho K.K., Japan) as follows. First, the photoreceptor was charged in the dark with −8 kV corona discharge. The resulting photoreceptor was exposed to white light at 3.0 lx to measure the time (sec) required for the surface potential to decrease to a half of the initial surface potential value. Thus, the half decay exposure, $E_{1/2}$ (lx·sec), was determined. This photoreceptor had an initial surface potential of −1,090 V and an $E_{1/2}$ of 1.7 lx·sec.

EXAMPLES 6 TO 18

Photoreceptor Nos. 2 to 14 were produced in the same manner as in Example 5, except that the charge generation material (Compounds A, B, C and D) and charge transporting material (hydrazone compound) were changed as shown in Table 5.

The results of the evaluation of photoreceptor Nos. 2 to 14 are given in Table 6.

TABLE 5

| Example No. | Photoreceptor No. | Charge Transporting Material Compound No. | Charge Generation Material Compound No. |
|---|---|---|---|
| 6 | 2 | 2 | A |
| 7 | 3 | 5 | A |
| 8 | 4 | 10 | B |
| 9 | 5 | 14 | B |
| 10 | 6 | 16 | B |
| 11 | 7 | 17 | A |
| 12 | 8 | 18 | A |
| 13 | 9 | 21 | A |
| 14 | 10 | 26 | B |
| 15 | 11 | 30 | B |
| 16 | 12 | 32 | B |
| 17 | 13 | 1 | C |
| 18 | 14 | 1 | D |

TABLE 6

| Photoreceptor No. | Initial Surface Potential (−V) | $E_{1/2}$ (lx · sec) |
|---|---|---|
| 2 | 1010 | 1.9 |
| 3 | 920 | 2.3 |
| 4 | 874 | 2.0 |
| 5 | 855 | 1.8 |
| 6 | 1005 | 1.8 |
| 7 | 1033 | 1.7 |
| 8 | 843 | 1.9 |
| 9 | 998 | 2.7 |
| 10 | 1220 | 1.9 |
| 11 | 980 | 2.1 |
| 12 | 1100 | 2.0 |
| 13 | 720 | 1.6 |
| 14 | 984 | 1.7 |

Compound B

Compound C

Compound D

EXAMPLE 19

To 50 parts of a 3% THF solution of a poly(vinyl butyral) resin (S-Lec BX-L, manufactured by Sekisui Chemical Co., Ltd., Japan) was added 1.5 parts of α-TiOPc as a charge generation material. This mixture was treated with an ultrasonic dispersing machine for 45 minutes to obtain a dispersion. An aluminum-deposited PET film serving as a conductive support was coated on the aluminum side with the above-obtained dispersion by means of a wire-wound bar coater. The coating was dried first at 60° C. and ordinary pressure for 2 hours and then at reduced pressure for 2 hours to form a charge generation layer having a thickness of 0.3 µm.

On the other hand, 1.5 parts of Compound No. 1 as a charge transporting material was added to 18.75 parts of an 8% dichloroethane solution of a polycarbonate resin (Panlite K-1300, manufactured by Teijin Chemicals Ltd.). Ultrasonic wave was applied to this mixture to completely dissolve the hydrazone compound.

This solution was applied to the charge generation layer with a wire-wound bar coater, and the coating was dried first at 60° C. and ordinary pressure for 2 hours and then at reduced pressure for 2 hours to form a charge transporting layer having a thickness of about 20 µm. Thus, photoreceptor No. 15 was produced.

The sensitivity of this photoreceptor was measured with an electrostatic copying paper tester (trade name "EPA-8100") as follows. First, the photoreceptor was charged in the dark with −8 kV corona discharge. The resulting photoreceptor was exposed to 800-nm monochromatic light at a light quantity of 0.4 µW/cm² to measure the quantity of energy required for the surface potential to decrease to a half of the initial surface potential value. Thus, the half decay exposure, $E_{1/2}$ (µJ/cm²), was determined. This photoreceptor had an initial surface potential of −1,085 V and an $E_{1/2}$ of 0.51 µJ/cm².

EXAMPLE 20

Photoreceptor No. 16 was produced in the same manner as in Example 19, except that the following trisazo compound was used as a charge generation material in place of α-TiOPc.

The sensitivity of this photoreceptor was measured in the same manner as in Example 19. As a result, this photoreceptor was found to have an initial surface potential of −1,125 V and an $E_{1/2}$ of 0.48 µJ/cm².

EXAMPLE 21

To 125 parts of an 8% dichloroethane solution of a polycarbonate resin (Panlite K-1300, manufactured by Teijin Chemicals Ltd.) were added 0.1 part of the following thiapyrylium salt as a charge generation material and 10 parts of Compound No. 18 as a charge transporting layer. Ultrasonic wave was applied to this mixture to completely dissolve the thiapyrylium salt and the hydrazone compound. An aluminum-deposited PET film serving as a conductive support was coated on the aluminum side with the above-obtained solution by means of a wire-wound bar coater. The coating was dried first at 60° C. and ordinary pressure for 2 hours and then at reduced pressure for 2 hours to form a photosensitive layer having a thickness of 15 µm. Thus, photoreceptor No. 17 was produced.

The sensitivity of this photoreceptor was measured with an electrostatic copying paper tester (trade name "EPA-8100") as follows. First, the photoreceptor was charged in the dark with +8 kV corona discharge. The resulting photoreceptor was exposed to white light at 3.0 lx to measure the time (sec) required for the surface potential to decrease to a half of the initial surface potential value. Thus, the half decay exposure, $E_{1/2}$ (lx·sec), was determined. This photoreceptor had an initial surface potential of +890 V and an $E_{1/2}$ of 2.8 lx·sec.

EXAMPLE 22

An aluminum-deposited PET film was coated on the aluminum side with the coating fluid of a charge transporting material which fluid had been used in Example 5, by means of a wire-wound bar coater. The coating was dried first at 60° C. and ordinary pressure for 2 hours and then at reduced pressure for 2 hours to form a charge transporting layer having a thickness of 10 µm.

On the other hand, 3.0 parts of the same disazo compound as used in Example 17 was added as a charge generation material to 18.5 parts of an 8% THF solution of a polyester resin (Vylon 200, manufactured by Toyobo Co., Ltd.). This mixture was placed in an agate pot containing agate balls, and this pot was rotated for 1 hour in a planetary grinder (manufactured by Fritsch Co.) to disperse the charge generation material. To this dispersion was added 200 parts of THF. The resulting mixture was stirred to give a coating fluid, which was then applied to the charge transporting layer by spraying. The coating was dried first at 60° C. and ordinary pressure for 2 hours and then at reduced pressure for 2 hours to form a charge generation layer having a thickness of 0.5 µm. This charge generation layer was further coated by spraying with a solution obtained by dissolving an alcohol-soluble polyamide resin in isopropanol. The coating was dried first at 60° C. and ordinary pressure for 2 hours and then at reduced pressure for 2 hours to form an overcoat layer having a thickness of 0.5 µm. Thus, photoreceptor No. 18 was produced.

The sensitivity of this photoreceptor was measured in the same manner as in Example 5. As a result, this photoreceptor was found to have an initial surface potential of +1,030 V and an $E_{1/2}$ of 2.2 lx·sec.

Comparative Example 1

A comparative photoreceptor was produced in the same manner as in Example 5, except that the following hydrazone compound was used in placed of Compound No. 1 used in Example 5.

The sensitivity of this photoreceptor was measured in the same manner as in Example 5. This photoreceptor had an initial surface potential of −970 V and an $E_{1/2}$ of 4.5 lx·sec. The results show that the hydrazone compound used, in which the hyrdazine moiety has a closed ring structure (i.e., $Ar_2$ and $R_3$ are bonded to each other to form a ring), has a low drift mobility and hence brought about the low sensitivity.

EXAMPLE 23

An ITO glass electrode (transparent conductive film of standard type; manufactured by Matsuzaki Shinku K.K., Japan) was set on the substrate holder of a vapor deposition device (Type LC-6F, manufactured by Shinku Kikai Kogyo K.K., Japan), and Compound No. 2 (4-[5-(10,11-dihydro-5H-dibenzo[b,f]azepinyl)]benzaldehyde N,N-diphenylhydrazone) was placed on the heating board. The vacuum chamber was evacuated to $1 \times 10^{-6}$ Torr. The heating board was heated and vapor deposition was conducted at a rate of 12 nm/min to form on the ITO glass electrode a 50 nm-thick hole-transporting layer made of Compound No. 2. Subsequently, tris(8-quinolinol)aluminum was placed on the heating board, which was then heated to conduct vapor deposition at a rate of 20 nm/min to form a 50 nm-thick luminescent layer on the hole-transporting layer. A 150 nm-thick magnesium layer was further formed thereon by vapor deposition at a rate of 40 nm/min, giving a counter electrode. Thus, an organic electroluminescent element was produced.

A 12-V direct current was applied to the element, with the ITO electrode as the positive electrode and the magnesium electrode as the negative electrode. As a result, the element emitted a bright green luminescence. The luminance of this light was measured with a luminance meter (Type LS-110, manufactured by Minolta Camera Co., Ltd., Japan), and was found to be 1,600 cd/m². A continuous illumination test was further performed at a luminance of 500 cd/m². As a result, the luminance half-life period of this element was 200 hours.

EXAMPLE 24

An organic electroluminescent element was produced in the same manner as in Example 23, except that Compound No. 17 (4-[5-(5H-dibenzo[b,f]azepinyl)]benzaldehyde N,N-methylphenylhydrazone) was used in place of Compound No. 2. A 13-V direct current was applied to this element. As a result, the element emitted a bright green luminescence at a luminance of 1,400 cd/m². A continuous illumination test was further performed at a luminance of 500 cd/m². As a result, the luminance half-life period of this element was 220 hours.

The novel hydrazone compound of the present invention has excellent hole-transporting ability and can be widely utilized as a hole-transporting material. The electrophotographic photoreceptor of the present invention having a photosensitive layer containing the hydrazone compound on a conductive support shows excellent photoreceptor properties and can be advantageously utilized widely as an electrophotographic photoreceptor. Furthermore, the organic electroluminescent element of the present invention produced using the hydrazone compound as a hole-transporting material, which compound forms a thermally stable satisfactory thin film, shows excellent luminescent properties and can be advantageously utilized widely as a display element.

While the invention has been described in detail and with reference to specific embodiments thereof, it will be apparent to one skilled in the art that various changes and modifications can be made therein without departing from the spirit and scope thereof.

What is claimed is:

1. A hydrazone compound represented by formula (I):

wherein $Ar_x$ represents a substituted or unsubstituted phenylene group, a substituted or unsubstituted naphthylene group, a substituted or unsubstituted biphenylene group, or a substituted or unsubstituted anthrylene group, $Ar_2$ represents a substituted or unsubstituted aryl group, $R_1$ and $R_2$ each independently represents a hydrogen atom, a halogen atom, an unsubstituted alkyl group, or an unsubstituted alkoxy group, $R_3$ represents an unsubstituted alkyl group, a substituted or unsubstituted aralkyl group, or a substituted or unsubstituted aryl group, Z represents an ethylene group or a vinylene group, and n is 0 or 1.

* * * * *